United States Patent [19]
Mantell

[11] Patent Number: 5,766,168
[45] Date of Patent: Jun. 16, 1998

[54] PERFORATED RESECTOSCOPE ELECTRODE ASSEMBLY

[75] Inventor: Robert Mantell, Arlington Heights, Ill.

[73] Assignee: Northgate Technologies, Inc., Elgin, Ill.

[21] Appl. No.: 585,308

[22] Filed: Jan. 11, 1996

[51] Int. Cl.$^6$ ............................................. A61B 17/36
[52] U.S. Cl. .................... 606/46; 606/41; 606/45; 606/49
[58] Field of Search ........................................ 606/32–52

[56] References Cited

U.S. PATENT DOCUMENTS

| | | | |
|---|---|---|---|
| 2,002,559 | 5/1935 | Wapple | 606/49 |
| 2,011,169 | 8/1935 | Wapple | 606/49 |
| 4,726,370 | 2/1988 | Karasawa et al. | |
| 5,007,907 | 4/1991 | Nishigaki et al. | |
| 5,196,011 | 3/1993 | Korth et al. | |
| 5,267,994 | 12/1993 | Gentelia et al. | |
| 5,462,521 | 10/1995 | Brucker et al. | 606/46 |
| 5,486,173 | 1/1996 | Vancaillie | |
| 5,549,605 | 8/1996 | Hahnen | |
| 5,569,244 | 10/1996 | Hahnen | |
| 5,573,535 | 11/1996 | Viklund | 606/41 |
| 5,582,610 | 12/1996 | Grossi et al. | 606/46 |

FOREIGN PATENT DOCUMENTS

| | | | |
|---|---|---|---|
| 9315664 | 8/1993 | WIPO | 606/46 |

*Primary Examiner*—David M. Shay
*Attorney, Agent, or Firm*—Brinks Hofer Gilson & Lione

[57] ABSTRACT

An improved electrode assembly for a resectoscope includes at least one electrical lead that connects at a proximal end via a handle of the resectoscope to an electrosurgical generator to receive electrical power. The electrode assembly further includes an electrode tip at a distal end. The electrode tip has a surface that includes at least one aperture and preferably multiple apertures that extend through the tip. The aperture serves to increase the area of the electrode tip relative to its mass thereby increasing the performance of the electrode for cutting, ablating, vaporizing, or coagulating tissue. The electrode tip performs these functions with relatively lower power requirements compared to conventional resectoscope electrodes.

22 Claims, 6 Drawing Sheets

PERFORATED RESECTOSCOPE ELECTRODE ASSEMBLY

BACKGROUND OF THE INVENTION

The present invention relates to resectoscopes and electrode assemblies for use therewith, and more particularly, the present invention relates to an improved electrode tip for an electrode assembly for an electrosurgical resectoscope.

Electrosurgical resectoscopes are used for transurethral and gynecological surgical procedures. Conventional electrosurgical resectoscopes include a handle, a telescope for viewing the surgical site and an electrode assembly that can be used for performing surgical procedures. A proximal portion of the electrode assembly is formed of an elongate conductor surrounded by an insulative sheath. A distal portion of the electrode assembly is typically formed by a pair of insulated wire leads. The proximal ends of the wire leads are connected to the distal end of the elongate conductor of the proximal portion of the electrode assembly. In one type of electrode assembly used for cutting, the distal ends of the leads are connected together in a wire loop. The wire loop is orthogonal to the axial direction of the electrosurgical resectoscope.

The resectoscope handle includes a connection for a cable that connects to an electrosurgical generator to receive power therefrom. The electrode assembly fits into a connection in the resectoscope handle to receive power from the generator. The electrosurgical generator provides electrical energy at power levels that are controllable by the physician.

Electrosurgical resectoscopes can be used for cutting, coagulating, vaporizing, or ablating. As mentioned above, in one type of electrode assembly for a conventional electrosurgical resectoscope, the wires at a distal end of the electrode assembly form a loop. The loop is used for cutting tissue under observation with the telescope. Other types of electrode assembly tips have been designed for use with electrosurgical resectoscopes. For example, one type of tip is formed of a solid sphere and another type of tip has a rotating barrel.

Conventional electrosurgical resectoscopes have numerous advantages. For example, conventional electrosurgical resectoscopes are relatively easy and economical to use compared to other types of surgical instruments, such as laser-based surgical tools. However, there are several aspects of conventional electrosurgical resectoscopes that limit their usefulness. For example, electrode assemblies are not relatively versatile. With a conventional electrosurgical resectoscope, if the physician desires to perform different types of procedures, such as cutting a tissue to obtain a sample and then ablating the area, the physician generally has to withdraw the electrosurgical resectoscope to replace the electrode assembly with another electrode assembly that has a different type of tip. Another disadvantage is that the electrode assembly tip can become clogged with tissue during use, thereby requiring the physician to remove the entire electrosurgical resectoscope to clean the tip of the electrode assembly.

Accordingly, there exists a need for a new resectoscope electrode with the capability of tissue vaporization, as well as cutting, coagulating, and ablating. Further, it would be desirable if an improved resectoscope electrode were available that could perform all of these activities in a single instrument.

SUMMARY OF THE INVENTION

According to one aspect of the present invention, there is provided an improved electrode tip for an electrode assembly for an electrosurgical resectoscope. The electrode assembly includes at least one electrical lead that connects at a proximal end via a handle to an electrosurgical generator to receive electrical power therefrom. The electrode tip has at least one perforation and preferably multiple perforations or apertures therethrough. The perforations may be slots or may be formed by shaping one or more wires to define one or more apertures through the electrode tip. The electrode tip is versatile so that the same tip can be used for cutting, vaporizing, ablating, and coagulating. A working surface of the electrode tip can be used for ablation or coagulation. The electrode tip also includes an edge that can be used for cutting.

According to a further aspect of the present invention, an electrode assembly for a resectoscope includes a tip with perforations that reduce the mass of the tip, thereby allowing for improved ablation at lower generator power levels, such as less than 200 watts. This compares favorably to the power levels required for other ablating instruments that require 250 watts or more.

DETAILED DESCRIPTION OF THE PREFERRED EMBODIMENTS

Figures 1, 2:
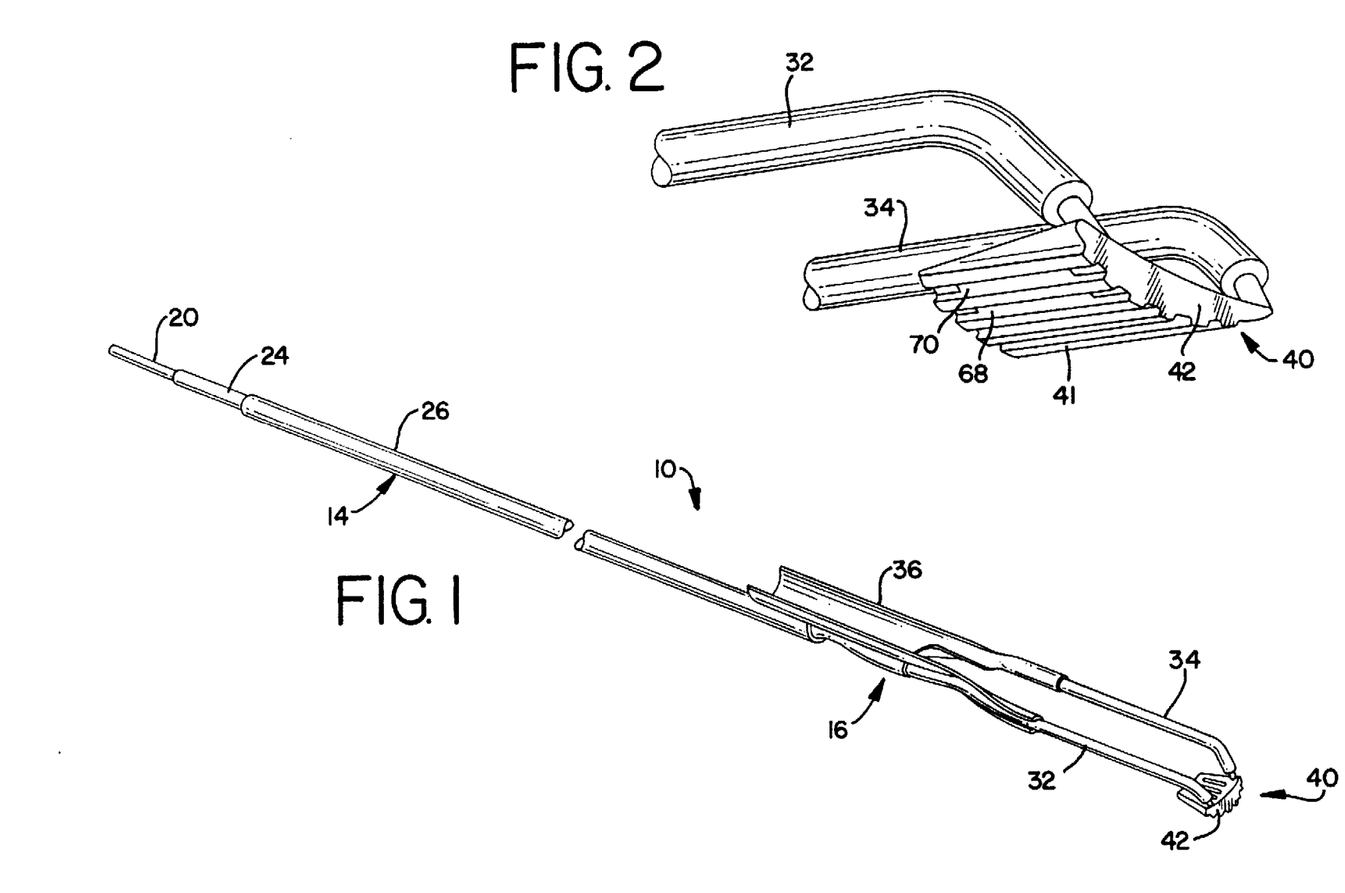
FIG. 1 is a perspective view showing a first embodiment of an electrode assembly for electrosurgical resectoscope.
FIG. 2 is a close up perspective view of the tip of the electrode assembly of FIG. 1.

FIG. 1 shows an electrode assembly 10 for an electrosurgical resectoscope. The electrode assembly 10 includes a proximal portion 14 and a distal portion 16. The proximal portion 14 includes a conductor 20 surrounded by an insulative plastic covering 24. The conductor 20 and covering 24 are enclosed by a rigid shaft 26. A proximal end 28 of the conductor 20 extends from the proximal end of the insulative covering 24 to form a connector pin which can be received in a jack on a conventional electrosurgical resectoscope handle (not shown). A proximal end of the insulative covering 24 extends from the proximal end of the rigid shaft 26.

The distal portion 16 of the electrode assembly 10 includes at least one, but preferably a pair of leads 32 and 34. Each of the leads includes an elongate conductor covered by an insulative covering. The proximal ends of the distal leads are connected electrically together to a distal end of the proximal conductor 20. The distal leads 32 and 34 diverge from each other distally of their proximal connection to the proximal conductor and extend parallel to each other to a distal end of the distal portion 16 of the electrode assembly 10. Located at the connection between the distal portion 16 and the proximal portion 14 is an elongate channel 36. The channel 36 is sized to receive the telescope portion (not shown) of the resectoscope as in a conventional resectoscope. The channel 36 is aligned to direct a resectoscope telescope between the parallel leads 32 and 34. At a distal end of the distal portion 16, the parallel leads angle downward to permit a telescope to extend distally past the distal end of the electrode assembly. The components of the electrode assembly described in detail so far may be manufactured according to conventional techniques using conventional materials.

The distal ends of the leads 32 and 34 both connect to a tip 40. The tip 40 is formed of an electrically conductive material so that the leads are connected together both mechanically and electrically. In this embodiment, the tip 40 is formed of a conductive block 42 having a chip-like shape. The tip may be made of any suitable conductive material such as a nickel-silver alloy, stainless steel, gold, tungsten, copper, or titanium.

Figure 3:
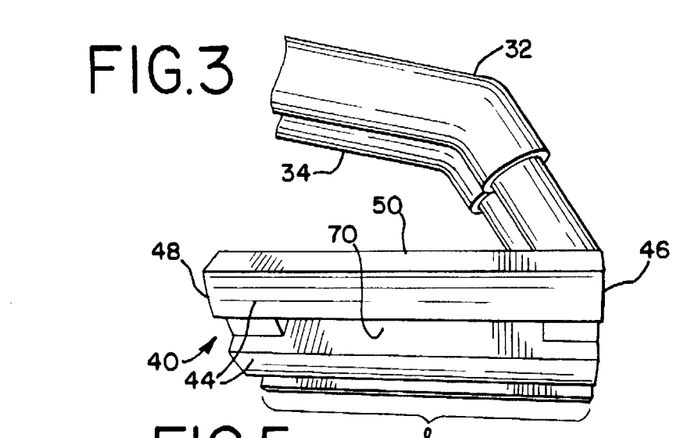
FIG. 3 is a side view of the tip of the electrode assembly shown in FIG. 2.
Figure 4:
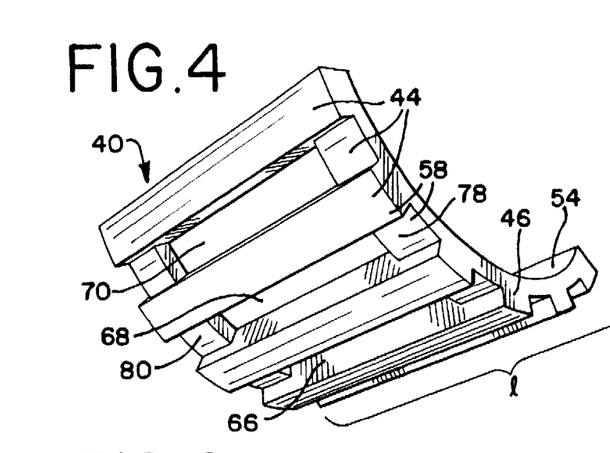
FIG. 4 is a bottom perspective view of the electrode assembly of FIG. 3 with the wire leads omitted for the sake of clarity.
Figure 5:
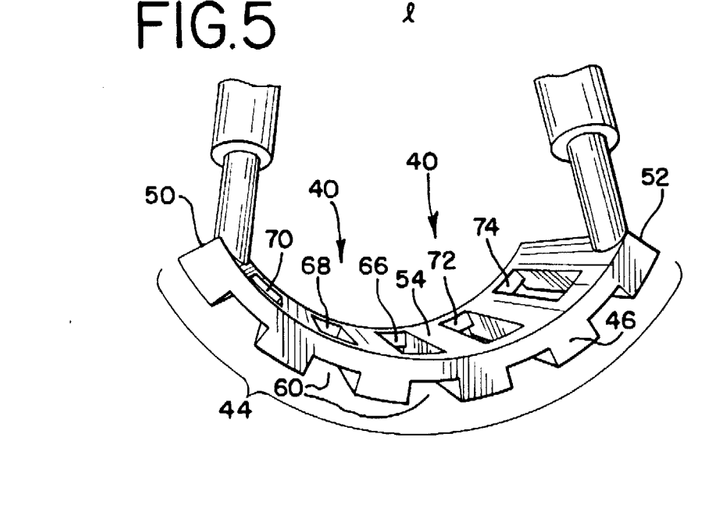
FIG. 5 is an end view of the electrode assembly of FIG. 2.

Referring to FIGS. 3–6, the tip 40 may be formed of a conductive block 42 and includes a working surface 44, a distal edge 46, a proximal edge 48, side edges 50 and 52, and an inner surface 54. As shown in FIG. 5, the working surface 44 is oriented in a direction away from the leads 32 and 34. The distal edge 46 of the tip 40 is located toward and faces the distal end of the electrode assembly 10 (FIG. 3). The proximal edge 48 is located opposite the distal edge 46 and faces toward the proximal end of the electrode assembly 10. The side edges 50 and 52 are located along horizontal or circumferential edges of the tip 40 (FIGS. 3–6). The inner surface 54 of the tip 40 is opposite the working surface 44 and oriented in a direction toward the leads 32 and 34 (FIG. 5).

The working surface 44 extends a length, 1, in a longitudinal (or axial) direction. In the embodiment shown, the length, 1, of the working surface 44 is approximately 5 mm. The distal edge 46 has a width, $w_1$, of approximately 5 mm and the proximal edge 48 has a width, $w_2$, of approximately 5 mm.

As shown in FIG. 3–6, the working surface 44 is relatively straight in the longitudinal direction and preferably has a convex curvature in a horizontal (or circumferential) direction. This horizontal curvature is provided so that the horizontal profile of the working surface 44 conforms generally to the shape of a conventional electrosurgical resectoscope sheath (not shown) through which the electrode assembly is introduced into the patient's body cavity. In a preferred embodiment, electrode assemblies may be provided in different sizes each having different working surface curvatures to accommodate different sizes of resectoscope sheaths.

As shown in FIG. 3, the tip 40 preferably has a shape that minimizes the mass of the tip. In one present embodiment, the tip is approximately 0.5 mm in thickness.

As mentioned above, the leads 32 and 34 connect to the inner surface 54 of the tip 40. Specifically, the leads 32 and 34 connect to the inner surface close to the corners at which the side edges 50 and 52 meet the distal edge 46. The leads 32 and 34 may be connected to the tip by any suitable means, such as soldering, welding, etc. The connection between the leads and the tip 40 is relatively rigid.

In the embodiment of FIGS. 1–6, the working surface 44 has a pattern 58 thereon. In the present embodiment, the pattern includes a plurality of grooves 60 or other surface configurations. These grooves 60 enhance the dissipation of current from the tip into the patient's tissue. Each groove is approximately 1 mm in width and 0.5 mm deep. The grooves 60 are evenly spaced and extend in the longitudinal direction from the distal edge 46 to the proximal edge 48.

The inner surface 54 is relatively smooth. In a present embodiment, it is preferred that the inner surface 54 have a concave contour that is similar to the contour of the working surface opposite thereto. The contour of the inner surface 54 provides for the tip having a relatively uniform thickness laterally and minimizes the mass of the tip.

Figure 6:
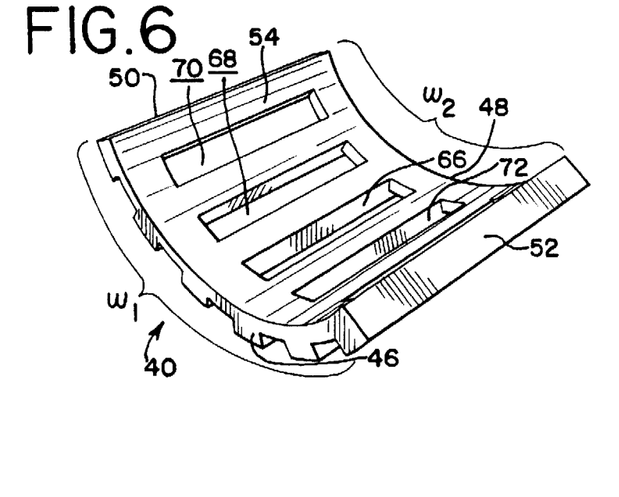
FIG. 6 is a top perspective view of the electrode assembly of FIG. 2 with the wire leads omitted for the sake of clarity.
Figure 7:
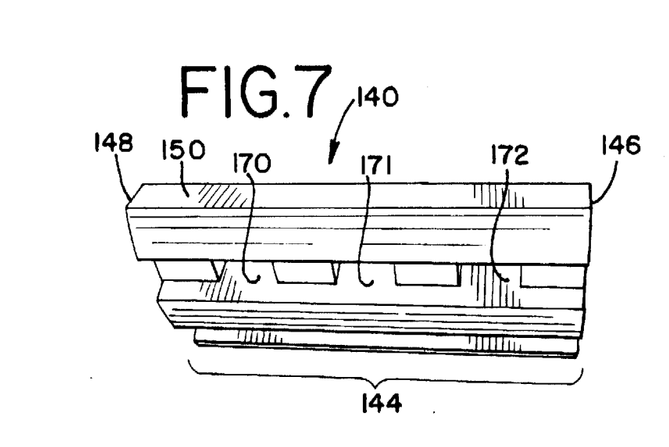
FIG. 7 is a side view similar to FIG. 3 showing a second embodiment of the electrode assembly tip of the present invention.
Figure 8:
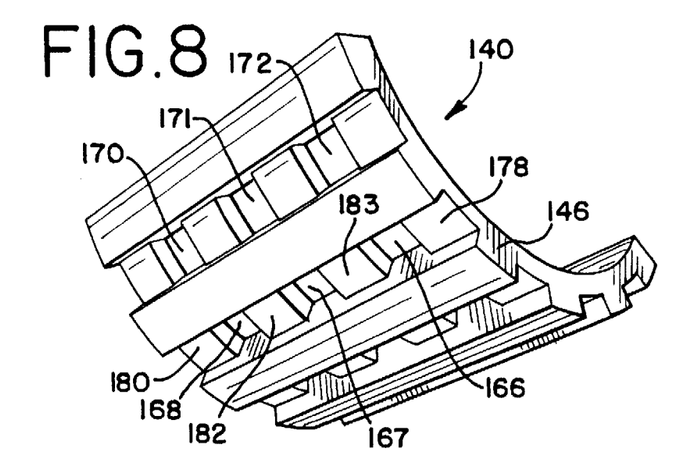
FIG. 8 is a bottom view of the embodiment of the electrode assembly tip shown in FIG. 7.
Figure 9:
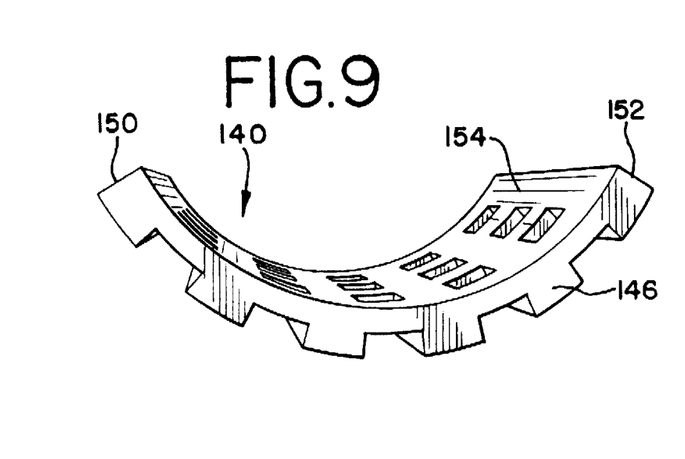
FIG. 9 is an end view of the embodiment of the electrode-assembly tip shown in FIG. 7.
Figure 10:
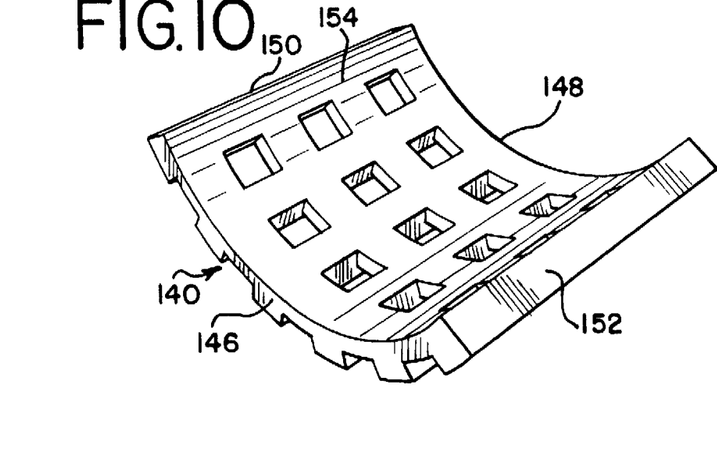
FIG. 10 is a top view of the embodiment of the electrode assembly tip shown in FIG. 7.
Figure 11:
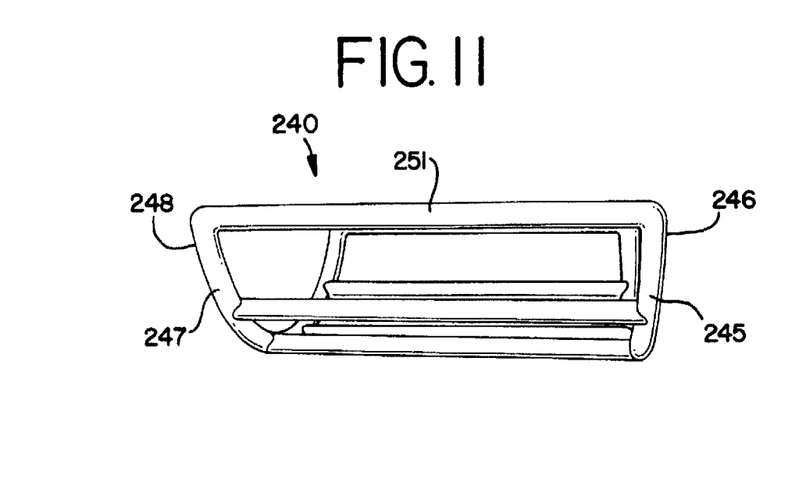
FIG. 11 is a side view similar to FIG. 3 showing a third embodiment of the electrode assembly tip of the present invention.
Figure 12:
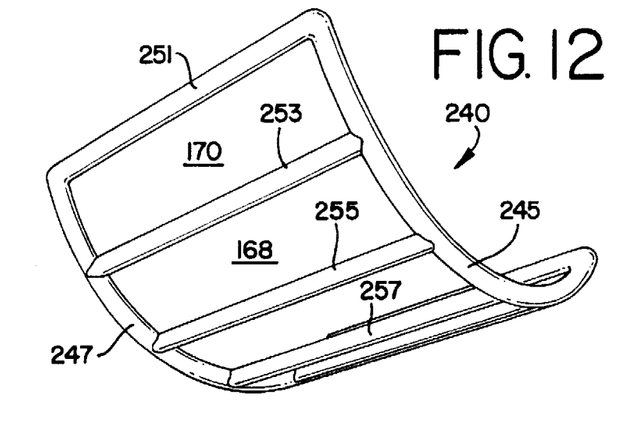
FIG. 12 is a bottom view of the embodiment of the electrode assembly tip shown in FIG. 11.
Figure 13:
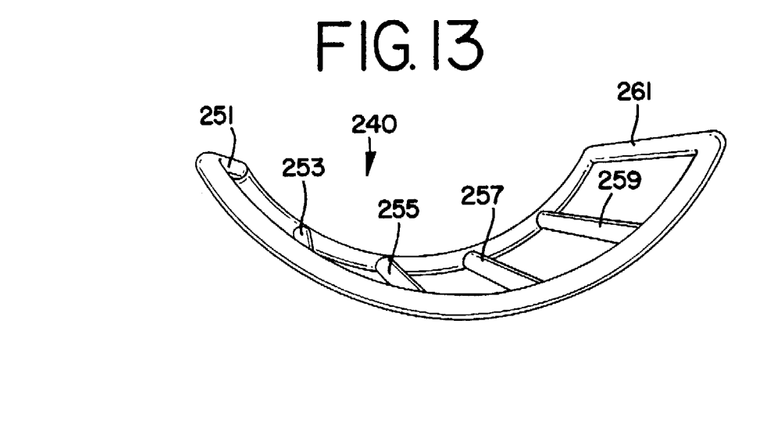
FIG. 13 is an end view of the embodiment of the electrode assembly tip shown in FIG. 11.
Figure 14:
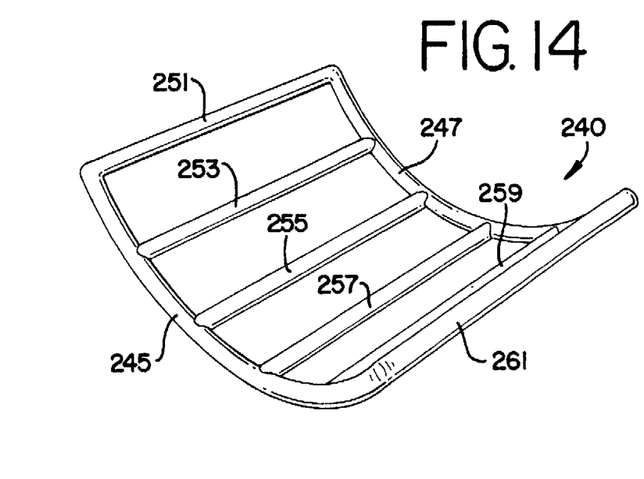
FIG. 14 is a top view of the embodiment of the electrode assembly tip shown in FIG. 11.
Figure 15:
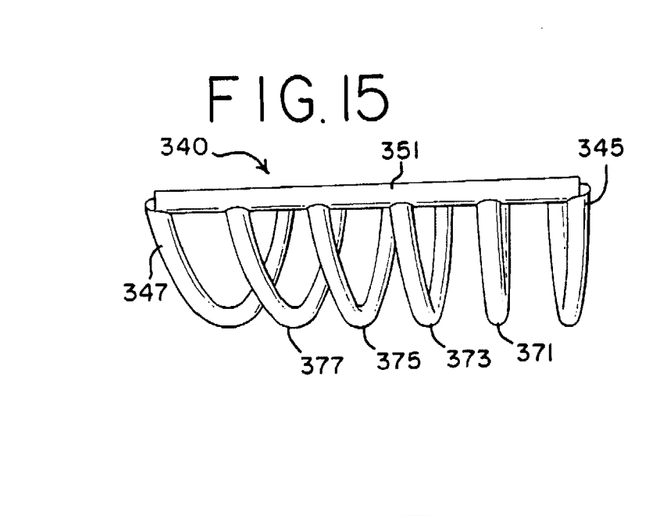
FIG. 15 is a side view similar to FIG. 3 showing a fourth embodiment of the electrode assembly tip of the present invention.
Figure 16:
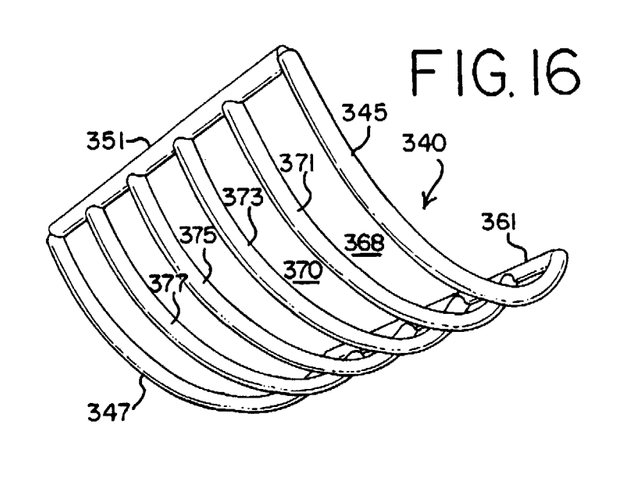
FIG. 16 is a bottom view of the embodiment of the electrode assembly tip shown in FIG. 15.
Figure 17:
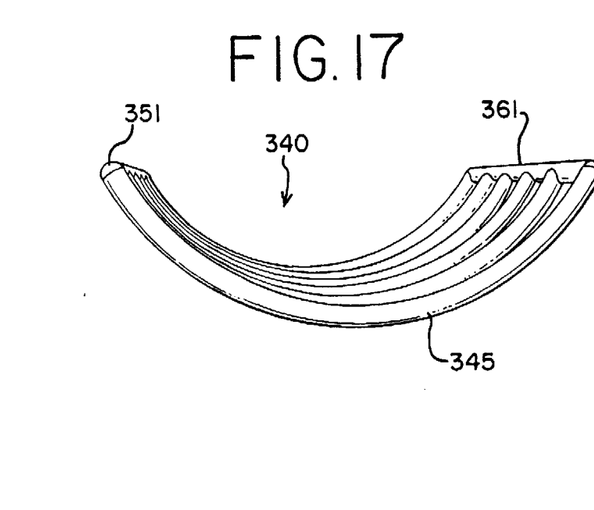
FIG. 17 is an end view of the embodiment of the electrode assembly tip shown in FIG. 15.
Figure 18:
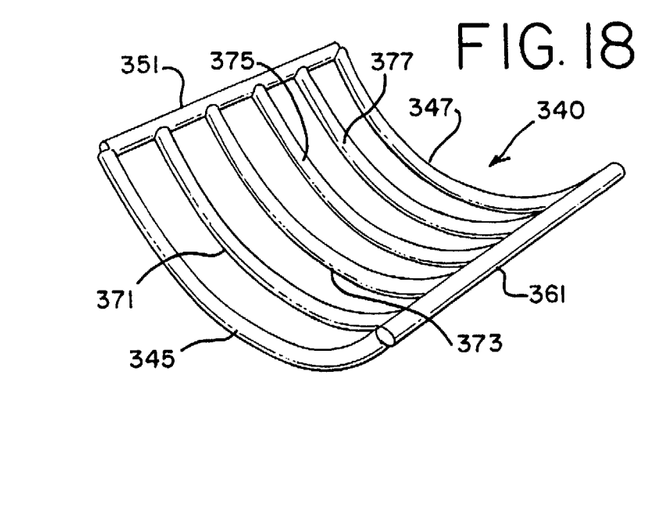
FIG. 18 is a top view of the embodiment of the electrode assembly tip shown in FIG. 15.
Figure 19:
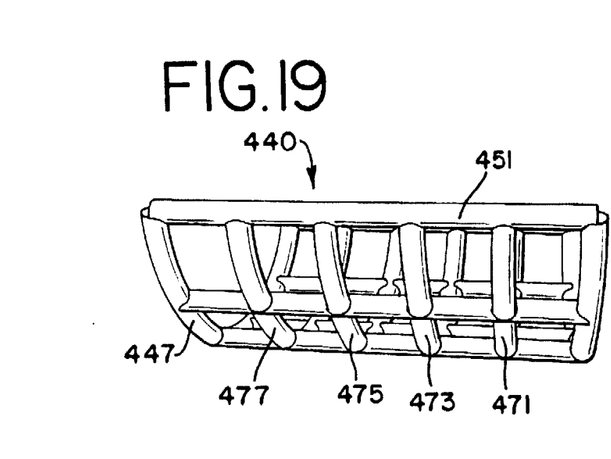
FIG. 19 is a side view similar to FIG. 3 showing a fifth embodiment of the electrode assembly tip of the present invention.
Figure 20:
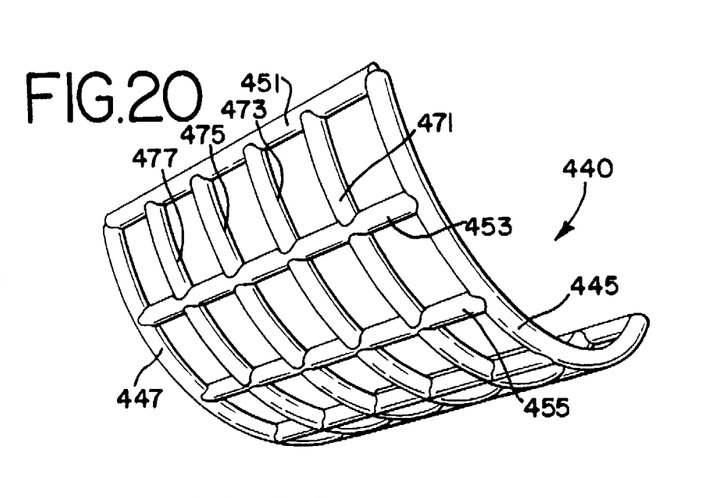
FIG. 20 is a bottom view of the embodiment of the electrode assembly tip shown in FIG. 19.
Figure 21:
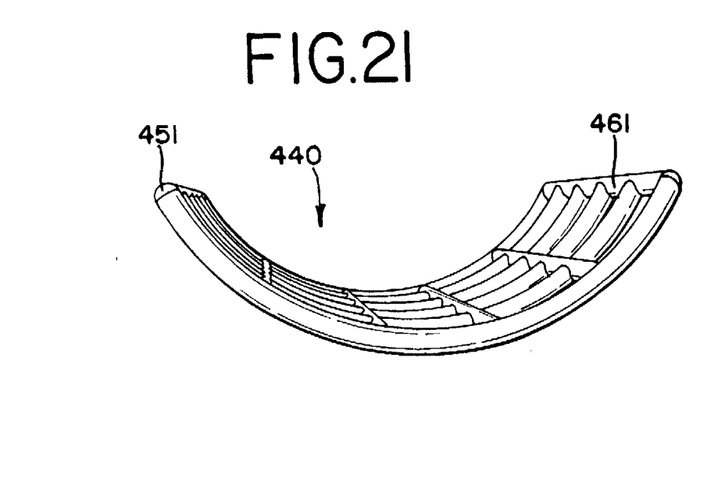
FIG. 21 is an en d view of the embodiment of the electrode assembly tip shown in FIG. 19.
Figure 22:
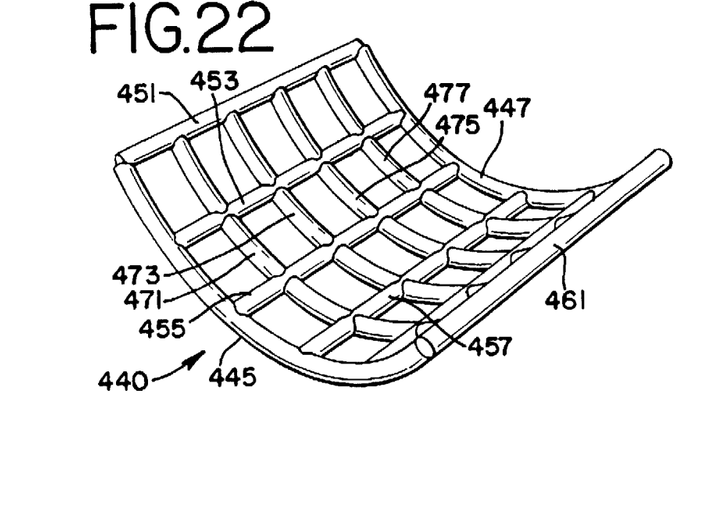
FIG. 22 is a top view of the embodiment of the electrode assembly tip shown in FIG. 19.

According to a present embodiment, the tip 40 has at least one perforation 66 and preferably multiple perforations 66, 68, 70, 72, and 74 therethrough. In this embodiment, the perforations 66–74 are slots that are located in the grooves 60. The slots extend in the same direction as the grooves 60 which in this embodiment also corresponds to the axial direction of the resectoscope assembly. Each slot extends substantially the entire length of its corresponding groove, but preferably does not extend to either the distal edge 46 or proximal edge 48 of the tip 40, leaving small sections (such as sections 78 and 80) of material at the distal and proximal edges of each groove.

The slots or apertures may be formed in the solid block 42 of the tip 40 by any suitable means, such as by machining, milling, laser cutting, casting, and any other suitable method for creating open areas in a solid piece.

The present embodiment of the electrode assembly is versatile and can be used by a physician for cutting, ablating, vaporizing, or coagulating. For example, to cut tissue, the physician assembles the resectoscope in a conventional manner and obtains access to the surgical site. The physician then advances the tip 40 around and distally past the tissue to be cut. Next, the physician sets the electrosurgical generator to a "cut" mode. Then, the physician brings the proximal edge 48 of the tip 40 into contact with the tissue to be cut and moves the electrode assembly in a proximal direction until the tissue is cut all the way through. The cut tissue may then be removed in a conventional way, such as by irrigating and flushing the area.

The present embodiment of the electrode assembly can also be used for ablating or vaporizing. To use the present embodiment for ablating, the same electrode assembly can be used as described above. The physician adjusts the electrosurgical generator to a suitable power level. For example, the generator may be set to the "cut" mode with the power adjusted appropriately. The physician then brings the working surface 44 of the tip 40 into contact with the area to be ablated. The working surface may be moved in any direction across the area to ablate the tissue in the area, as desired.

The present embodiment can also be used for coagulation. To coagulate an area, the physician sets the generator to the appropriate mode, such as the "coag" mode. The power level in this mode is relatively lower than in the "cut" mode. The physician brings the working surface 44 into contact with the area to be coagulated.

The electrode assembly as described above enables a physician to perform a variety of common procedures with the same electrode assembly thereby obviating the need to withdraw the resectoscope to change the electrode tip. Thus, the present embodiment of the electrode assembly facilitates efficiency and may reduce costs by eliminating the need to use a variety of electrode assemblies.

An alternative embodiment of the electrode tip 140 is shown in FIGS. 7–10. This embodiment is similar to the previously described embodiment and like components are identified with like numbers, incremented by 100. This embodiment of the electrode tip differs from the previous embodiment in the pattern of perforations in the tip 140. In the embodiment of FIGS. 7—10, the perforations 166, 167, 168, 170, 171, 172 form an array of perforations. This array of perforations may be formed by including a plurality of perforations, such as perforations 166, 167, and 168, in each of a plurality of grooves, as shown in FIGS. 7–10. Each perforation may be approximately 0.5 mm in size. In the embodiment of FIGS. 7–10, the perforations are approximately evenly spaced. As in the previous embodiment, sections of material, such as 178 and 180, separate a perforation from the distal and proximal edges of the tip. In addition, sections of material, such as 182 and 183, separate each of the perforations from each other. As in the previous embodiment, the multiple perforations enhance the performance of the electrode tip by providing a greater surface area from which current can enter into tissue.

FIGS. 11–14 show a third embodiment of the present invention. This embodiment is similar to the previously described embodiments and like components are identified with like numbers incremented by 200 relative to the embodiment of FIGS. 1–6. This embodiment of the electrode tip differs from the previous embodiments in that the electrode tip 40 is not formed by a solid block 11 of material through which one or more apertures are formed. Instead, the embodiment of FIGS. 11–14 is formed by one or more wires connected together to form the tip 240. A distal end wire 245 and a proximal end wire 247 have curved shapes that define the curved contour of the electrode assembly 240. A plurality of relatively straight parallel wires 251, 253, 255, 257, 259, and 261, extend in the longitudinal direction of the electrode assembly 240 and connect to the distal and proximal end wires 245 and 247. The plurality of wires form a grid with relatively large apertures or perforations, 168, 170, extending therethrough. The wires forming the electrode assembly tip may be connected together by weaving, soldering, welding, adhesives, or other suitable means, or alternatively, the wire grid may be formed by other processes, such as by extrusion, stamping, molding, etching, wire extruding, or other processes.

FIGS. 15–18 show a fourth embodiment of the present invention. This embodiment is similar to the previously described embodiment and like components are identified with like numbers incremented by 100 relative to the embodiment of FIGS. 11–14. Like the previous embodiment, the electrode tip 340 is formed by one or more wires connected together to form the tip 340. A distal end wire 345 and a proximal end wire 347 have curved shapes that define the curved contour of the electrode assembly 340. Relatively straight parallel wires 351 and 361 extend in the longitudinal direction of the electrode assembly 340 and connect to the distal and proximal end wires 345 and 347. These straight parallel wires, 351 and 361, form the side edges of the tip 340. This embodiment differs from the previous embodiment in the direction of the parallel wires that make up the wire grid of the electrode assembly. In the embodiment of FIGS. 15–18, the plurality of parallel wires 371, 373, 375, and 377 have a similar curved shape as the wires 345 and 347. The parallel wires 371, 373, 375, and 377 connect to the side edge wires 351 and 361 to form a grid with relatively large apertures or perforations, 368, 370, extending horizontally across the tip. The wires forming the electrode assembly tip may be connected together by the means described above.

FIGS. 19–22 show a fifth embodiment of the present invention. This embodiment of the electrode tip 440 is similar to the previously described embodiment and like components are identified with like numbers incremented by 100 relative to the embodiment of FIGS. 15–18. Like the previous embodiments, the electrode tip 440 is formed by one or more wires connected together to form the tip 440. A distal end wire 445 and a proximal end wire 447 have curved shapes that define the curved contour of the electrode assembly 440. Relatively straight parallel wires, 451 and 461, extend in the longitudinal direction of the electrode assembly 440 and connect to the distal and proximal end wires 445 and 447. These straight parallel wires, 451 and 461, form the side edges of the tip 440. This embodiment of the electrode tip includes two groups of parallel wires that make up the wire grid of the electrode assembly. In the embodiment of FIGS. 19–22, a first group of plurality of parallel wires 471, 473, 475, and 477 have curved shapes that are similar to the wires 445 and 447. This first group of parallel wires is parallel to the distal and proximal end wires 445 and 447. A second group of parallel wires, 453, 455, 457, and 459, extend in the longitudinal direction of the electrode assembly 440 and are parallel to the edge wires 451 and 461. All the wires interconnect to form a grid with apertures or perforations extending therethrough. The wires forming the electrode assembly tip may be connected together by the means described above.

Each of the above disclosed embodiments of the resectoscope electrode tip provides an extended active area for energy to be distributed to patient tissue. This active area is preferably highly conductive to promote the transfer of the energy to the patient's tissue. The active area preferably also has minimal mass. In order to provide efficient transfer of energy without unnecessary resistance caused by the solid working element, the tip includes either holes, slots, apertures, perforations, etc. These may be formed either by making slots or hole patterns within the working element, or by creating a wire weave, mesh, matrix, etc., out of a conductive material.

As illustrated by the embodiments of the resectoscope electrode assembly disclosed above, the resectoscope electrode working element may have any of several various shapes or geometries. For example, the working element may have a curved shape, as shown in the drawings. In addition, the working element may have various other shapes, such as a flat, spherical, half-moon, wedge, etc. These embodiments of the electrode assembly may have a shape such that when retracted into the resectoscope, the electrode tip fits snugly into the contour of the scope to allow tissue to be pushed off the working element. The working element may cover a significant amount of tissue area (at least approximately 20 square mm), but it can be as large as can reasonably be used in the resectoscope. The working element preferably has slots or holes to reduce its mass and loss of energy, yet maximize the number of surface points from which energy can be transferred. Also, it is preferable that the working element has an edge suitable for cutting tissue as it is resecting.

The embodiments of resectoscope electrode assemblies disclosed are capable of accomplishing all the usual types of operations, e.g. cutting, coagulating, ablating, and vaporizing. In addition, the embodiments of the electrode tip use less energy more in the range of conventional cutting loops. Thus, embodiments of the electrode assembly may utilize currently available electrosurgical generators (e.g. Electro-Surgical units) rather than requiring higher powered units (250 to 300 watts). The embodiments of the electrode assembly may also cause less bleeding by the patient especially compared to conventional ablating roller devices, thereby providing for safer procedures with fewer complications, and faster procedure times. Fewer electrodes may be used since there would be no need for a separate ablating electrode and a cutting electrode. The embodiments of the electrode assembly are less expensive to use than laser-based surgical techniques.

It is intended that the foregoing detailed description be regarded as illustrative rather than limiting and that it is understood that the following claims including all equivalents are intended to define the scope of the invention.

I claim:

1. An electrode assembly for resectoscope, comprising:
   at least one electrical lead having a proximal end that connects to an electrosurgical generator to receive electrical power therefrom; and
   an electrode tip connected to a distal end of said at least one electrical lead, said electrode tip having a distal edge, a proximal cutting edge, and two side edges bounding a substantially flat working surface exgtending in a longitudinal direction, said surface including at least one perforation extending therethrough.

2. The electrode assembly of claim 1 wherein said surface includes a pattern thereon.

3. The electrode assembly of claim 2 wherein said pattern comprises a plurality of grooves.

4. The electrode assembly of claim 3 wherein said perforation is located in one of said plurality of grooves.

5. The electrode assembly of claim 3 wherein said plurality of grooves includes a plurality of perforations.

6. The electrode assembly of claim 3 wherein at least some of said plurality of grooves include a plurality of perforations.

7. In a resectoscope having an electrode assembly that connects to a source of electrical energy, said electrode assembly having an elongate shaft and at least one electrical lead extending along said elongate shaft, said electrical lead having a proximal end that receives electrical energy from said source, the improvement comprising:
   an electrode tip coupled to a distal end of said elongate shaft and electrically connected to said electrical lead, said electrode tip having a distal edge, a proximal edge, and two side edges bounding a substantially flat working surface that extends in a longitudinal direction and further wherein said working surface includes at least one aperture therethrough, and further wherein said proximal edge is tapered to form a cutting surface.

8. The invention of claim 7 wherein said tip is formed of a wire weave.

9. The invention of claim 1 wherein the tip is composed of a material selected from a group consisting of: nickel silver, stainless steel, tungsten, copper, titanium, and gold.

10. The invention of claim 7 wherein said tip is formed of a plurality of parallel wires.

11. The invention of claim 10 wherein said parallel wires extend in a direction parallel to an axial direction of the electrode assembly.

12. The invention of claim 10 wherein said parallel wires extend in a direction orthogonal to an axial direction of the electrode assembly.

13. The invention of claim 10 wherein said parallel wires comprise a first group of parallel wires that extend in a direction parallel to an axial direction of the electrode assembly and a second group of parallel wires that extend in a direction orthogonal to the axial direction.

14. The invention of claim 7 wherein said tip includes multiple apertures.

15. The invention of claim 14 wherein said apertures extend substantially an entire length of said tip.

16. The invention of claim 14 wherein said multiple apertures are arranged in an array.

17. The invention of claim 14 wherein said multiple apertures comprise parallel elongate slots.

18. The invention of claim 17 wherein said parallel slots extend in a direction parallel to an axial direction of said electrode assembly.

19. The invention of claim 14 wherein said tip includes a plurality of grooves and further wherein said apertures are located in said plurality of grooves.

20. The invention of claim 19 wherein multiple apertures are located in at least some of the grooves.

21. An improved electrode assembly for a resectoscope, wherein said electrode assembly includes a conductor extending from a connector at a proximal end, wherein said improvement comprises:
   a tip connected to a distal end of said conductor, said tip comprising a substantially flat working surface, said working surface extending in a longitudinal direction and having a distal edge, a proximal cutting edge, and two side edges surrounding said substantially flat working surface, and further wherein said substantially flat working surface has a plurality of holes located therethrough.

22. The improved electrode assembly of claim 21 wherein said working surface has grooves thereon.

* * * * *

UNITED STATES PATENT AND TRADEMARK OFFICE
CERTIFICATE OF CORRECTION

PATENT NO. : 5,766,168
DATED : June 16, 1998
INVENTOR(S) : Robert Mantell

It is certified that error appears in the above-identified patent and that said Letters Patent is hereby corrected as shown below:

On the Title Page

In column 1, line 1, under "U.S. PATENT DOCUMENTS", please change "Wapple" to --Wappler--.

In column 1, line 2, under "U.S. PATENT DOCUMENTS", please change "Wapple" to --Wappler--.

In the Claims

In claim 1, line 8, please change "exgtending" to --extending--.

Signed and Sealed this

Fifth Day of September, 2000

Attest:

Q. TODD DICKINSON

Attesting Officer

Director of Patents and Trademarks